United States Patent [19]

Agrawal et al.

[11] Patent Number: 5,321,131
[45] Date of Patent: Jun. 14, 1994

[54] SITE-SPECIFIC FUNCTIONALIZATION OF OLIGODEOXYNUCLEOTIDES FOR NON-RADIOACTIVE LABELLING

[75] Inventors: Sudhir Agrawal, Shrewsbury; Jinyan Tang, Worcester, both of Mass.

[73] Assignee: Hybridon, Inc., Worcester, Mass.

[21] Appl. No.: 490,481

[22] Filed: Mar. 8, 1990

[51] Int. Cl.$^5$ .............................................. C07H 21/00
[52] U.S. Cl. ................................ 536/25.34; 536/23.1; 536/25.32; 536/25.33; 435/6
[58] Field of Search ............................. 536/27, 28, 29

[56] References Cited

U.S. PATENT DOCUMENTS

| | | | |
|---|---|---|---|
| 4,547,569 | 10/1985 | Letsinger et al. | 536/25.32 |
| 4,762,779 | 8/1988 | Snitman | 435/6 |
| 4,837,312 | 6/1989 | Dervan et al. | 536/25.32 |
| 4,958,013 | 9/1990 | Letsinger | 536/24.9 |
| 4,959,463 | 9/1990 | Froehler et al. | 536/25.3 |
| 4,965,349 | 10/1990 | Woo et al. | 536/25.3 |

OTHER PUBLICATIONS

Nevinskii et al., Chemical Abstracts: vol. 99, No. 5, 35050n, Aug. 1, 1983.
Dobronravova et al., Chemical Abstracts: vol. 98, No. 7, 54383u, Feb. 14, 1983.
Cardullo et al., Proc. Natl. Acad. Sci. USA 85:8790-8794 (1988).
Haralambidis et al., Nucleic Acids Res. 18:501-505 (1990).
Helene & Toulme, *Oligonucleotides.* Ed. Cohen, MacMillan Press, pp. 137-167 (1989).
Matthews & Kricka, Analytical Biochem. 169:1-25 (1988).
Nelson et al., Nucleic Acids Res. 17:7187-7194 (1989).
Zwierzak, A., Communications. 507-509 (1975).
Froehler & Matteucci, Nucleic Acids Res. 16:4831-4839 (1988).
Letsinger et al., J. Am Chem. Soc. 110:4470-4471 (1988).
Jager et al., Biochemistry. 27:7237-7246 (1988).
Caruthers et al., Methods in Enzymology. 154:287-313 (1987).
Agrawal et al., Nucleic Acids Res. 14:6227-6245 (1986).
Le Doan et al., Nucleic Acids Res. 15:8643-8659 (1987).
Agrawal & Goodchild, Tetrahedron Lett. 28:3539-3542 (1987).
Agrawal et al., Proc. Natl. Acad. Sci. USA, 85:7079-7083 (1988).
Agrawal, S., Tetrahedron Lett. 30:7025-7028 (1989).
Fidanza & McLaughlin, J. Am. Chem. Soc. 111:9117-9119 (1989).
Haralambidis et al., Nucleic Acids Res. 18:493-499 (1990).
Agrawal et al. J. Cell Biology 107:468-483 (1988).

*Primary Examiner*—Johnnie R. Brown
*Assistant Examiner*—J. Oliver Wilson
*Attorney, Agent, or Firm*—Lappin & Kusmer

[57] ABSTRACT

Disclosed are compounds consisting of a plurality of nucleosides which are covalently linked by at least one aminoalkylphosphoramidate linkage of the formula $$Nu_2-O-\underset{\underset{NH(CH_2)_nNH}{|}}{\overset{\overset{O}{\|}}{P}}-O-Nu_1$$

wherein n=2 to 6 and $Nu_1$ and $Nu_2$ represent nucleoside phosphates.

1 Claim, 2 Drawing Sheets

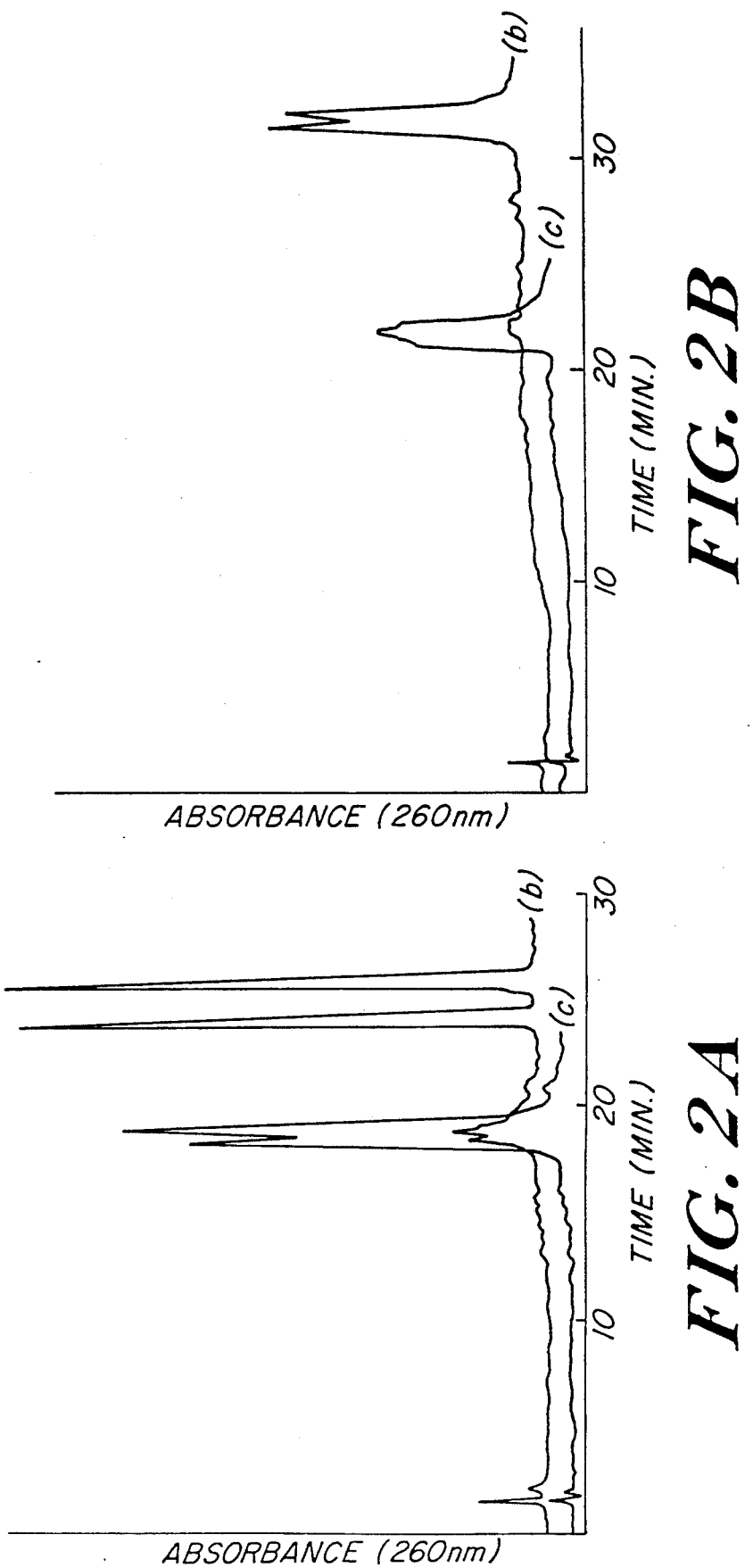

SITE-SPECIFIC FUNCTIONALIZATION OF OLIGODEOXYNUCLEOTIDES FOR NON-RADIOACTIVE LABELLING

FUNDING

Work described herein was supported by cooperative grant U01 124846 from the National Institute of Allergies and Infectious Disease and a grant from the G. Harold and Leila Y. Mathers Foundation.

BACKGROUND OF THE INVENTION

There is at present growing interest in non-radioactively labelled modified oligodeoxynucleotides. Biotin (Agrawal. S. et al., *Nucleic Acid Research*, 14:6227–6245 (1986); Agrawal, S. *Tet. Lett.*, 30:7025–7028 (1989)), florophores (Cardullo, R. A. et al., *Proc. Natl. Acad. Sci. USA*, 85:8790–8794 (1988); Agrawal, S. et al., *J. Cell Biology*, 107:468 (1988); Haralambidis, J. et al., *Nucleic Acids Res.*, 18(3):501–505 (1989)), intercalating (Helene, C. and J. J. Toulme, *Oligodeoxynucleotides-Antisense Inhibitors of Gene Expression*, Ed. J. S. Cohen, Macmillan Press, 137–166 (1989)) and chelating (Oser, A. et al., G. *Nucleic Acid Research*, 16:1181–1196 (1988)) reagents attached to synthetic oligonucleotides are becoming important tools of molecular biology. A variety of enzymatic and chemical procedures have been developed for their synthesis (Matthews, J. S. and L. J. Kricka, *Anal. Biochem.*, 169:1–25 (1988)). Central to some of these procedures are (a) the introduction of a reactive group at either the 3'- or 5'- terminus of the oligonucleotide (Agrawal. S. et al., *Nucleic Acid Research*, 14:6227–6245 (1986); Agrawal, S. *Tet. Lett.*, 30:7025–7028 (1989); Fidanza, J. A. and L. W. McLaughlin, *J. Am. Chem. Soc.*, 111:9117–9119 (1989); Nelson, P. S. et al., *Nucleic Acid Research*, 17:7187–7194 (1989)) or (b) the synthesis of modified nucleosides which contain the masked reactive group and are incorporated into the nucleic acid (Fidanza, J. A. and L. W. McLaughlin, *J. Am. Chem. Soc.* 111:9117–9119 (1989)). The presently-available methods are useful, but are limited in their usefulness for site specific internal non-radioactive labelling of synthetic oligonucleotides possible.

SUMMARY OF THE INVENTION

The present invention relates to a method of site specific functionalization of oligodeoxynucleotides for non-radioactive labelling, as well as to functionalized oligodeoxynucleotides and non-radioactively labelled oligodeoxynucleotides produced by the method. This method makes it possible to modify one or more selected internucleoside phosphate(s) in a synthetic oligodeoxynucleotide in such a manner that it (they) can be used to incorporate a non-radioactive material into the synthetic oligodeoxynucleotide. In particular, the method of the present invention is used to modify one or more selected internucleoside phosphates in a synthetic oligodeoxynucleotide, to give aminoalkylphosphoramidate residues or aminoalkylphosphotriester residues. The amino group(s) of the resulting modified residue(s) is then further reacted with a non-radioactive label, such as biotin, fluorescein or rhodamine (e.g., N-hydroxysuccinimide ester of biotin, N-caproyl amidobiotin, and a variety of fluorophore isothiocyanates), to produce a non-radioactively labelled oligodeoxynucleotide in which the label is present at a predetermined location or locations.

In the present method, an H-phosphonate internucleoside linkage is oxidized with an appropriately protected diamine, such as N-1-trifluoroacetylhexanediamine, ($CF_3CO\ NH(CH_2)_6NH_2$), in the presence of an appropriate solvent, such as carbon tetrachloride, to give a phosphoramidate internucleoside linkage (Zwierzak, A., *Synthesis*, 507–508 (1975); Froehler, B. et al., *Nucleic Acid Research*, 16:4831–4839 (1989); Letsinger, R. L. et al., *J. Am Chem. Soc.*, 110:4470–4471 (1988); Agrawal, S. et al., *Proc. Natl. Acad. Sci. USA*, 85:7070–7083 (1988); Jager, A. et al., *Biochemistry*, 27:7237–7246 (1988)). The resulting phosphoramidate internucleoside linkage is stable under oligonucleotide assembly conditions using phosphoramidite chemistry (Caruthers, M. H. et al., *Methods in Enzymology*, 154:287–313 (1987)) and to subsequent deprotection steps. Alternatively, the H-phosphonate internucleoside can be oxidized, to give a phosphotriester internucleoside linkage, with an appropriately protected aminoalkyl alcohol in N-methylimidazole-triethylamine-carbon tetrachloride (e.g., 5:5:90).

The present method can be used to produce non-radioactively labelled oligodeoxynucleotides which include a non-radioactive material at one or more sites and are useful in research and in the diagnosis and treatment of diseases and conditions of interest.

BRIEF DESCRIPTION OF THE DRAWINGS

FIG. 2A is a graphic representation of the results of reversed phase HPLC traces of oligomer 2 (chromatogram (a)), and reaction mixture of oligomer with biotin N-hydroxysuccinimide (chromatograph (b)); and FIG. 2B is a graphic representation of the results of reversed phase HPLC traces of oligomer 5 (chromatograph (c)) and reaction mixture of oligomer 5 with biotin N-hydroxysuccinimide (chromatograph (d)).

DETAILED DESCRIPTION OF THE INVENTION

Figure 1B:
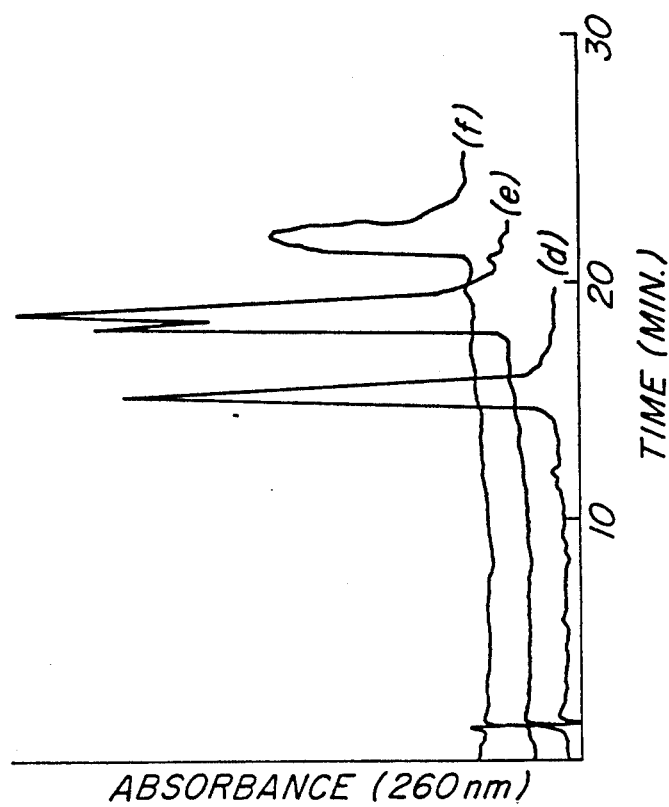
FIG. 1B is a graphic representation of the results of reversed phase HPLC of ion exchange purified oligomers 1 (chromatograph (d)), 2 (chromatograph (e)), and 3 (chromatograph (f))

The present invention relates to a method of producing oligodeoxynucleotides which have a desired (selected) nucleotide sequence and which are labelled internally with a non-radioactive material or reporter group at one or more internucleoside linkages. In the method of the present invention, one or more selected internucleoside phosphate residues are modified to produce aminoalkylphosphoramidate residues or aminoalkylphosphotriester residues which are present in an oligodeoxynucleotide at selected positions. The amino group(s) in such modified (functionalized) residues is further reacted with a label or reporter group, resulting in production of a non-radioactively labelled oligodeoxynucleotide labelled internally at selected location(s).

Briefly, the present method is carried out by oxidizing an H-phosphonate internucleoside linkage using an appropriately protected diamine, represented by the formula $XCONH(CH_2)_nNH_2$, in which X is a base labile protecting group and n can be 2 or more. For example, an H-phosphate internucleoside linkage is oxidized using N-1-trifluoroacetylhexanediamine ($CF_3CONH(CH_2)_6NH_2$) in the presence of an appropriate solvent, such as anhydrous carbon tetrachloride. As a result, a primary aliphatic amine is incorporated at the internucleoside phosphate as phosphoramidate. In the case of phosphotriester linkages, oxidation is carried out using a suitably protected amino alcohol, represented by the formula $XNH(CH_2)_nOH$, in which X is a base labile protecting group and n can be 2 or more. For example, an H-phosphonate internucleoside linkage is oxidized using N-1-fluoroenylmethyoxcarbonylaminohexanol F-MOC-$NH(CH_2)_6OH$ in the presence of N-methylimidazole-triethylamine-carbon tetrachloride. The remaining nucleotides needed to produce the desired nucleotide sequence are added using art-recognized techniques, such as phosphoramidate, H-phosphonate chemistry or methyl phosphoramidate. (Caruthers, M. H. et al., *Methods in Enzymology*, 154:287–313 (1987); co-pending U.S. patent application Ser. No. 07/334,679 (Method of Synthesizing Oligonucleotides and Their Analogs Adaptable to Large Scale Synthesis, by S. Agrawal and P. Zamecnik, filed Apr. 6, 1989, the teachings of which are incorporated herein by reference; Agrawal, S. and J. Goodchild *Tet. Lett.*, 28(31):3539–3542 (1987)). After the desired oligodeoxynucleotide is produced, the protecting group present on the primary aliphatic amine is removed. The unmasked amino group can now react with one or more selected labels or reporter groups. As a result, the oligodeoxynucleotide is labelled, non-radioactively, at one or more selected internal locations. One or both amino groups present in the diamine react with the selected label.

The method of the present invention is represented in a series of steps below. The following is an explanation of those steps, with reference to the respective reactants and steps represented below.

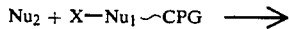

(I)

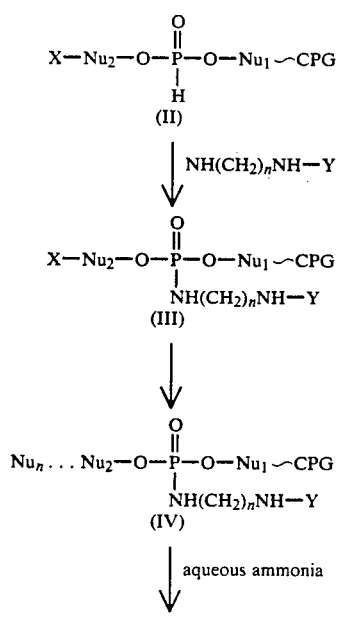

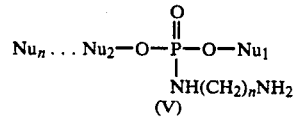

(V)

1. Initial coupling of two nucleotides (designated $Nu_1$ and $Nu_2$) is carried out, using H-phosphonate chemistry. Generally, $Nu_1$ is bound to a solid support, such as CPG and terminates in a diemthoxytrityl residue (designated X). As a result, a support-bound dinucleoside H-phsophonate is produced (designated (II)).

2. The support-bound dinucleoside H-phosphonate (II) is subsequently oxidized by being combined with an appropriately protected diamine in the presence of a suitable solvent, resulting in formation of a phosphoramidate internucleoside linkage or a phosphotriester internucleoside linkage (and linking of the protected diamine to the dinucleoside through the unprotected amino group of the diamine). The resulting product is designated (III).

3. The dimethoxytrityl residue present on the unbound end of (I) is removed and the remaining deoxynucleotides of the desired oligodeoxynucleotide to be produced are added at the now free end, using phosphoramidate chemistry or H-phosphonate chemistry, producing a support-bound oligodeoxynucleotide (IV) which includes the phosphoramidate linkage produced in step (2).

4. The protecting group Y present on the diamine is removed and the compound is removed from the solid support. This results in production of an unbound functionalized oligodeoxynucleotide (i.e., an aminoaliphatic oligomer or an oligodeoxynucleotide having a desired nucleotide sequence and an alkyl amino group present at the selected internucleoside phosphate(s) as a phosphoramidate or phosphotriester).

5. The unbound functionalized oligodeoxynucleotide is reacted with an appropriate form of a non-radioactive material, which becomes bound to the amino group and serves as a label or reporter group on the oligodeoxynucleotide. This results in production of an oligodeoxynucleotide labelled site specifically with a non-radioactive material. The non-radioactive material can be a fluorophore, a spin label, an enzyme, a chelator, a heterocyclic molecule, a protein, a lipid, a drug derivative, an antigen, an intercalator or other organic or inorganic moiety.

In a specific embodiment of the present invention, which has been used to produce non-radioactively labelled oligodeoxynucleotides, the following steps were carried out to produce a non-radioactively labelled oligodeoxynucleotide:

1. Initially, (I) and $Nu_2$ were coupled, using art-recognized H-phosphonate chemistry, resulting in production of a support-bound dinucleoside H-phosphonate.

2. The support-bound dinucleoside H-phosphonate was oxidized, using N-1-trifluoroacetyldiaminohexane ($NH(CH_2)_6NH\text{-}CO\text{-}CF_3$) in carbon tetrachloride-dioxane, resulting in formation of a phosphoramidate internucleoside linkage between $Nu_2$ and $Nu_1$.

3. The remainder of the nucleotide sequence of the oligodeoxynucleotide was produced in a two-step procedure in which the dimethoxytrityl residue [DMTrO] was removed from the nucleotide now bound to the solid support ($Nu_2$ in the reaction scheme above) and the desired nucleotides were added stepwise (i.e., to the now free end of the dinucleoside which, for convenience, can be referred to as the 5' end).

4. The protecting group (-CO-CF$_3$) present on NH(CH$_2$)$_6$NH-CO-CF$_3$ was removed during deprotection of oligonucleotides in aqueous ammonia, resulting in production of a functionalized oligodeoxynucleotide (one in which the previously protected amino group is unprotected) of the desired sequence, in which there is an aminoalkylphosphoramidate residue of the formula $$O=\overset{|}{\underset{|}{P}}-NH(CH_2)_6NH_2$$

present at the desired internucleoside phosphate linkage(s).

5. The unbound modified oligodeoxynucleotide with the aminoalkylphosphoramidate residue was reacted with a non-radioactive material, such as biotin, fluorescein or rhodamine in appropriate form (e.g., N-hydroxysuccinimide ester of biotin, N-caproyl amidobiotin, fluorophore isothiocyanates), which becomes bound to the amino group of the aminoalkylphosphoramidate internucleoside linkage.

Alternatively, a functionalized oligodeoxynucleotide of the desired sequence, in which there is an aminoalkylphosphotriester residue present at the desired internucleoside phosphate linkage(s) can be produced. In this case, the non-radioactive material becomes bound to the amino group of the aminoalkylphosphotriester internucleoside linkage.

The production of oligodeoxynucleotides labelled at a selected site or sites by the present method is described in greater detail in the Exemplification.

It is possible, using the present method, to produce oligodeoxynucleotides of desired sequence which are labelled internally at one or more nucleosides. The oligodeoxynucleotide backbone can be unmodified (e.g., as it occurs in nature) or modified (e.g., amidate, methylphosphate, phosphothioate, phosphotriester backbones). The label present at two or more sites can be the same (e.g., biotin) or different and can be present at as many sites as desired. As described in the Exemplification, a 17-met of the sequence shown has been produced, functionalized at a selected site or sites and labelled at the site(s) with a non-radioactive material.

In the above description of the present method, two single nucleotides (designated Nu$_1$ and Nu$_2$) are initially joined using H-phosphonate chemistry and the resulting oligodeoxynucleotide is functionalized at the internucleoside phosphate linkage formed between Nu$_1$ and Nu$_2$. However, any number of nucleotides can be joined, using art-recognized techniques such as H-phosphonate chemistry, before modification of a selected internucleoside phosphate linkage is carried out. This has been carried out, as described in the Exemplification, to produce a 17-mer functionalized at a central internal site (oligomer 3) and a 17-mer functionalized at two internal phosphate linkages (oligomer 5). Using H-phosphonate chemistry, for example, an internal nucleotide (e.g., a support-bound nucleotide such as Nu$_1$) can be added to, resulting in production of a longer sequence (e.g. Nu$_{10}$Nu$_9$ . . . Nu$_1$). The longer sequence can then be functionalized, by the method described above, resulting in production of a functionalized oligodeoxynucleotide (e.g., Nu$_{10}$ ↓ Nu$_9$ . . . Nu$_1$, in which the internucleoside phosphate linkage between Nu$_9$ and Nu$_{10}$ is modified). The modified oligodeoxynucleotide can then be further elongated by addition of selected nucleotides to produce a modified oligodeoxynucleotide of desired sequence. The protecting group present can be removed, as described above. Alternatively, the functionalized oligodeoxynucleotide initially produced can be extended (by addition of selected nucleotides), one or more additional internucleoside phosphate linkages can be modified and a functionalized oligodeoxynucleotide which has two or more sites at which non-radioactive material can be added is, thus, produced.

Protecting groups other than trifluoroacetyl (—CO—CF$_3$), as described above, can also be used to protect the diamine. Other base labile protecting groups, such as F-moc and t-boc, may also be used. The linker present between the two amino groups in the diamine used can be of any suitable length (e.g., —(CH$_2$)$_2$— to —(CH$_2$)$_n$—); the length used in a particular case can be determined empirically. The diamine can be branched or unbranched and bi-functional or multifunctional.

EXEMPLIFICATION

Preparation of N-1-trifluoroacetylhexanediamine and Its Use for Site-Specific Introduction of Amino Groups into Oligodeoxynucleotides N-1-trifluoroacetylhexanediamine, CF$_3$CONH(CH$_2$)$_6$NH$_2$, was prepared by adding ethyltrifluoroacetate (1.2 ml, 10 mmol) dropwise over one hour to a stirred mixture of hexanediamine (1.16g; 10 mmol) and triethylamine (1 ml; 7 mmol) in 20 ml methanol. The solution was stirred overnight. After removal of solvents, the reaction mixture was flash chromatographed on silica using 0-25% methanol in dichloromethane. The fractions containing the desired product were pooled and concentrated to give a colorless powder (1.1 gm, yield-42.6%), M.pt. 52°. $^1$NMR (CDCl$_3$, d, TMS=0.00) 7.1-7.2 (m 3H, NH$_2$, NH) 3.2-3.3 (m 2H CO-NH-CH$_2$) 2.8-2.9 (m 2H CH$_2$-NH$_2$) 1.2-1.6 (m 8H - CH$_2$ - ( CH$_2$ )$_2$-CH$_2$).

To test the efficacy of (CF$_3$CONH(CH$_2$)$_6$NH$_2$) for amino group introduction at specific sites of oligonucleotides, a 17-mer sequence, GTA AAA CGA CGG CCA GT, (oligomer 1) was made. Oligomers (designated 2-5 below) carrying aminohexyl residues at different sites, as shown by ( ↓ ), were also made.

| Oligomer # | Sequence |
|---|---|
| 1 | GTA AAA CGA CGG CCA GT |
| 2 | GTA AAA CGA CGG CCA G ↓ T |
| 3 | GTA AAA CG ↓ A CGG CCA GT |
| 4 | G ↓ TA AAA CGA CGG CCA GT |
| 5 | G ↓ TA AAA CGA CGG CCA G ↓ T |

The steps involved for labelling, for sequence 2, are shown below:

DMTrO—T ~ CPG 

(I)

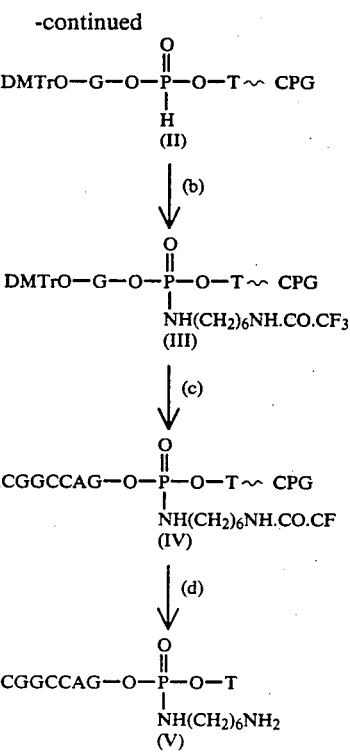

The first coupling (represented by (a) in the above reaction) was carried out using H-phosphonate chemistry. This resulted in a production of a support-bound dinucleoside H-phosphonate (II), which was then oxidized with 4% N-1-trifluoroacetyldiaminohexane (I) in carbon tetrachloride-dioxane (8:2, v/v) for 30 minutes, resulting in production of (III). After oxidation with $CF_3CONH(CH_2)_6NH_2$ (step (b) of the above reaction), the assembly of the rest of the oligodeoxynucleotide sequence was carried out (step (c)) using phosphoramidite or H-phosphonate chemistry. This resulted in production of the oligonucleotide (IV), which was deprotected in aqueous ammonia for 6 hours at 55° C. (step (d)), resulting in formation of the aminohexyl oligomer (V).

Assessment of the oligomers 1–5 was carried out. Analytical ion exchange HPLC of oligomer 2 showed the major peak eluting earlier than that of oligomer 1 with the same gradient (FIG. 1a and 1b), confirming that in oligomer2, one of the internucleoside linkages is a phosphoramidate linkage, which is non-ionic at phosphores. Sequences 3 and 4, which are functionalized at different sites, also showed a HPLC profile similar to that of oligomer 2. Oligomer 5, which is functionalized at two sites, was eluted even earlier (FIG. 1A, chromatograph (c)).

Figure 1A:
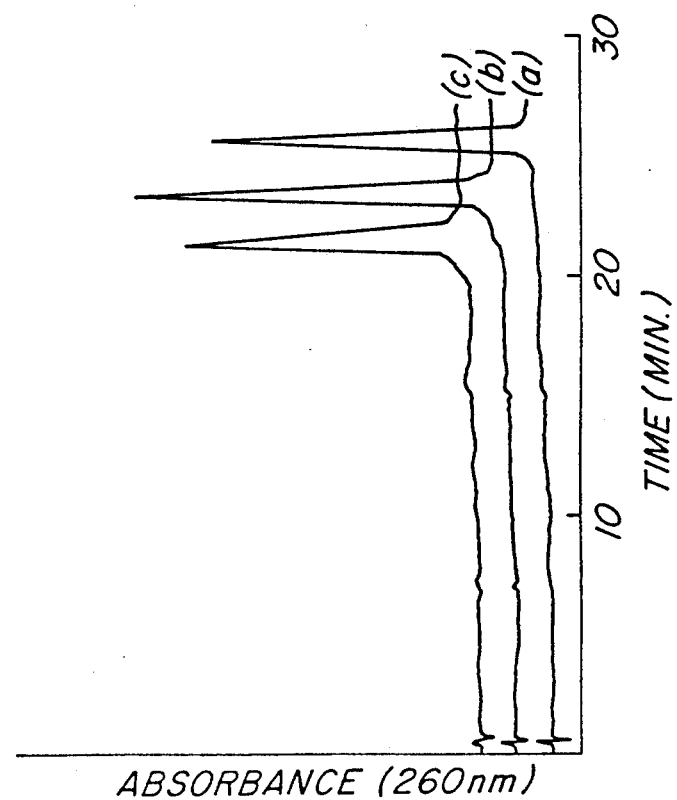
FIG. 1A is a graphic representation of the results of analytical ion exchange HPLC of oligomers 1 (chromatograph (a)), 2 (chromatograph (b)), and 5 (chromatograph (c))

When ion exchange HPLC purified oligomer 2 was checked on reversed phase HPLC, it gave a doublet peak in ratio of 1:2 (FIG. 1A, chromatograph (e)) compared to 1 (FIG. 1A, chromatograph (d)). This results from the diastereoisomeric nature of phosphoramidate internucleoside linkage. Similarly, oligomer 5 eluted as a broad peak because of two such diastereoisomeric linkages (FIG. 1f). Both oligomers 2 and 5 had retention times longer than that of oligomer 1 because of the hydrophobic nature of the alkyl chain present in oligomers 2 and 5.

Reaction of oligomer 2 was carried out with biotin N-hydroxysuccinimide using reported conditions (Agrawal, S. et al., *Nucleic Acid Research*, 14:6227–6245 (1986)). The reaction mixture after gel filtration (Sephadex G-25) showed two new peaks of the diastereomeric biotin adducts (FIG. 2A, chromatograph (b)). Similarly, reaction of oligomer 5 gave a broad peak ass a doublet eluting later than the unreacted material (FIG. 2B, chromatographs (c) and (d)).

The method described herein provides a way for functionalizing oligonucleotides at one or more selected or specified sites. As described above, the subject method of introducing reporter groups has been carried out by reaction of the functionalized oligodeoxynucleotide with biotin active ester, resulting in production of an oligodeoxynucleotide labelled at the selected site(s) with biotin. In addition, the aminohexyl residue present was reacted in high yield with fluorescein and rhodamine isothiocyanate, to produce a fluorescent hybridization probe. Multiple labelling may increase the sensitivity of detection in diagnostic assays.

Equivalents

Those skilled in the art will recognize, or be able to ascertain using no more than routine experimentation, many equivalents to the specific embodiments of the invention described specifically herein. Such equivalents are intended to be encompassed in the scope of the following claims.

We claim:
1. A compound consisting of a plurality of nucleosides selected from the group consisting of adenosine, thymidine, cytosine, and guanosine, wherein the nucleosides are covalently linked by mono-phosphodiester bonds and one or two aminoalkylphosphoramidate linkages of the formula:

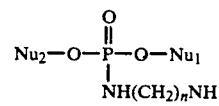

wherein n is 6, and
Nu$_1$ and Nu$_2$ represent nucleoside phosphates wherein the nucleosides are as stated above, and wherein Nu$_1$+Nu$_2$ is 17 nucleotides.

* * * * *

UNITED STATES PATENT AND TRADEMARK OFFICE
CERTIFICATE OF CORRECTION

PATENT NO. : 5,321,131
DATED : June 14, 1994
INVENTOR(S) : Sudhir Agrawal and Jinyan Tang It is certified that error appears in the above-indentified patent and that said Letters Patent is hereby corrected as shown below:

On the title page: Item [73]

Assignee should be changed from "Hybridon, Inc., Worcester, Mass." to --The Worcester Foundation for Experimental Biology, Shrewsbury, Mass.--

Signed and Sealed this

Twentieth Day of December, 1994

Attest:

BRUCE LEHMAN

*Attesting Officer*          *Commissioner of Patents and Trademarks*